(12) United States Patent
Anninou et al.

(10) Patent No.: US 7,258,659 B2
(45) Date of Patent: Aug. 21, 2007

(54) ELECTRONIC DEVICE FOR STRENGTHENING THE IMMUNE SYSTEM

(76) Inventors: Nicolia Anninou, 4 Alexandrou Panagouli, Alexandroupolis (GR) 68100; Ioannis Tsagas, Opisthen N.E. Katikies, Xanthi (GR) 67100

( * ) Notice: Subject to any disclaimer, the term of this patent is extended or adjusted under 35 U.S.C. 154(b) by 218 days.

(21) Appl. No.: 10/522,033

(22) PCT Filed: Jul. 22, 2003

(86) PCT No.: PCT/GB03/00031

§ 371 (c)(1),
(2), (4) Date: Jan. 21, 2005

(87) PCT Pub. No.: WO2004/011093

PCT Pub. Date: Feb. 5, 2004

(65) Prior Publication Data

US 2006/0058572 A1  Mar. 16, 2006

(30) Foreign Application Priority Data

Jul. 25, 2002  (GR)  ............................. 20020100362

(51) Int. Cl.
*A61N 1/00*  (2006.01)
(52) U.S. Cl. .......................................... 600/13; 600/15
(58) Field of Classification Search ............. 600/9–15; 607/1–2, 65; 324/244
See application file for complete search history.

(56) References Cited

U.S. PATENT DOCUMENTS

| | | | |
|---|---|---|---|
| 4,428,366 A * | 1/1984 | Findl et al. .................... | 600/14 |
| 4,889,526 A * | 12/1989 | Rauscher et al. .............. | 600/14 |
| 5,444,373 A * | 8/1995 | Johnson et al. .............. | 324/248 |
| 5,453,072 A * | 9/1995 | Anninos et al. ................ | 600/9 |
| 5,496,258 A * | 3/1996 | Anninos et al. .............. | 600/13 |
| 6,527,697 B2 * | 3/2003 | Bashford et al. ............. | 600/13 |

FOREIGN PATENT DOCUMENTS

| | | |
|---|---|---|
| DE | 28 21 114 A | 11/1978 |
| DE | 44 40 898 A | 5/1996 |
| DE | 198 34 148 A | 2/2000 |
| WO | WO99 01178 | 1/1999 |
| WO | WO 01 15770 A | 3/2001 |

* cited by examiner

*Primary Examiner*—Charles A. Marmor, II
*Assistant Examiner*—Christine D. Hopkins
(74) *Attorney, Agent, or Firm*—Dowell & Dowell P.C.

(57) ABSTRACT

One electronic device proper for strengthening the immune system, produces magnetic fields with characteristics which are determined by a multi channel biomagnetometer. The electronic device is including an alternating current output generated by a microcontroller of symmetric square wave signals with a specific frequency which is regulated by one integrated circuit which receives the frequency value from a keyboard or from a computer through a serial port and an interface integrated circuit and supplies a great number of coils, up to 122, with hemispheric or plane arrangement for the production of symmetric square wave signal of magnetic fields. The electronic device is including also a liquid crystal display and a crystal of high constant oscillation for timing of the system. The strengthening of the immune system is accomplished with the decomposing removal of all placed complex inorganic substances from the glands of the brain with the help of the spiral oscillations of the plasma ions in the blood and this results to energize these glands for better hormone production and activation of the brain.

18 Claims, 2 Drawing Sheets

ELECTRONIC DEVICE FOR STRENGTHENING THE IMMUNE SYSTEM

BACKGROUND OF THE INVENTION

1. Field of the Invention

The present invention relates to an electronic device for strengthening of the immune system with the use of magnetic fields the characteristics of which are determined by multi channel biomagnetometer. The electronic device employs a microcontroller for producing an alternating current of regulated specific frequency which supplies a great number of coils, about 122, in a specific hemispheric or plane arrangement, in order to cover the whole brain or other parts of the body, for the production of alternating symmetrical magnetic fields of positive symmetrical square wave signal. The intensity and frequency of the alternating current is regulated with a specific binary system according to the frequency and intensity which are determined during the diagnosis with the 122 multi channel biomagnetometer. The strengthening of the immune system is accomplished with the removal of the calcium and other similar chemical elements from the pineal gland and other brain glands. With this removal is accomplished better action and function of the glands for the production of inhibitory hormones, as is the melatonin, which are necessary for the removal of the free radicals which are produced during oxidation. The removal of the inorganic substances from the glands is accomplished with the help of the spiral oscillations of the electrical charged plasma ions in the brain around and along the magnetic lines of the alternating magnetic field. In addition it can be accomplished better adjustment in the ion concentrations which are necessary for better neuronal function.

2. Prior Art

There is no relevant bibliography existing in prior art with respect to the strengthening of the immune system with the influence of magnetic fields.

SUMMARY OF THE INVENTION

The first object of the present invention is to provide an electronic device which helps the strengthening of the immune system with the influence of alternating magnetic fields of special form and specific frequency and intensity which are determined with the use of the multi channel biomagnetometer, microcontroller for producing an alternating current of square wave signal and low frequency supplies through resistors a great number of coils, up to 122, which are in specific hemispheric or plane arrangement, in order to cover the whole brain or other parts of the body, for the production of alternating magnetic fields of positive symmetrical square wave signal with 50% duty cycle. These magnetic fields force the charged plasma ions, according to the alpha rhythm frequency of each individual, in spiral oscillations around the magnetic lines of square form. The above ions decompose and remove the complex inorganic substances from the brain glands and this has as a result to activate and to energize these glands for better hormone production, as for example the melatonin which is produced by the pineal gland, which are useful for the immune system and for the neurons. The decrease of melatonin concentration is related with many dysfunctions of the organism.

A second object of this invention is to provide an electronic device to produce very low magnetic fields as is the intensity, the wave signal and the frequency which are emitted from each person and they are determined with magnetoencephalographic measurements by the multi channel biomagnetometer, which is based on the superconductivity of some specific substances in very low temperatures. Every change in the magnetic field is measured by the biomagnetometer as a current which can be interpreted from it as a potential difference which can be amplified and measured properly.

The above mentioned objects of the present invention are implement with the use of an electronic device to produce magnetic fields with the characteristics of the magnetic fields which have measured from the brain with the multi channel biomagnetometer, are alternating of square wave signal with intensity of the order of some pT and of low frequency up to 15 Hz. The device is able to produce similar magnetic fields from a large number of coils, up to 122, which are in hemispheric or plane arrangement so that to cover all 5 brain regions or other parts of the body. The positive symmetrical square wave signal has given the best results.

BRIEF DESCRIPTION OF THE DRAWINGS

The application of the invention is described below by reference to the accompanying drawings wherein the above mentioned objects and other novel features of this invention will become apparent to those skilled in the art.

DETAILED PRESCRIPTION OF PREFERRED EMBODIMENTS

Figure 1:
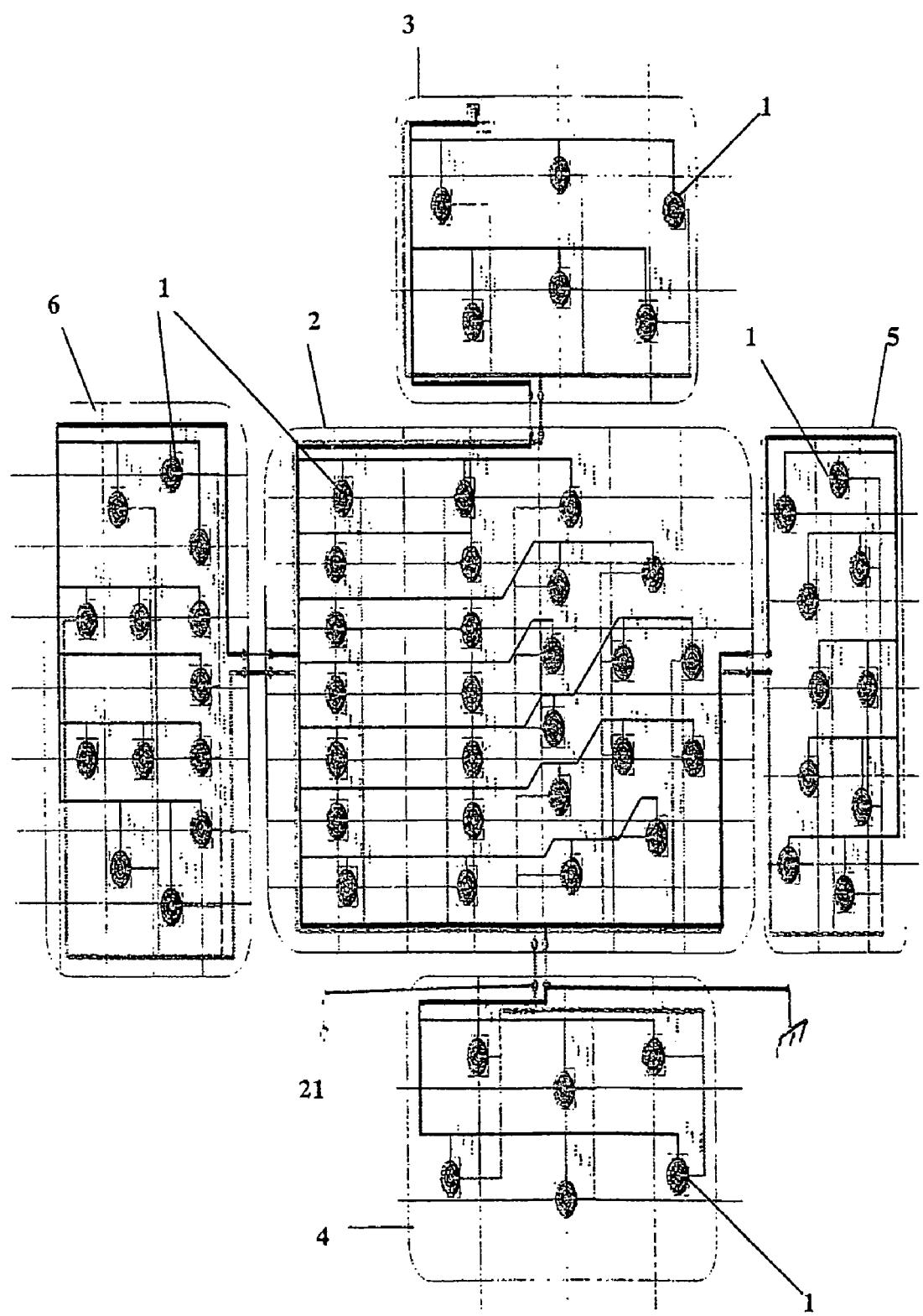
FIG. 1 shows a perspective view of five groups of 61 coils of spiral form wherein the groups of coils of the device in accordance with the present invention are in hemispheric or plane arrangement so that to cover the five brain regions of the skull or other parts of the body. All the coils are connected in parallel through resistors with an alternating current output and produce all the coils similar magnetic fields with similar characteristics. The number of coils can be increased up to 122.
Figure 2:
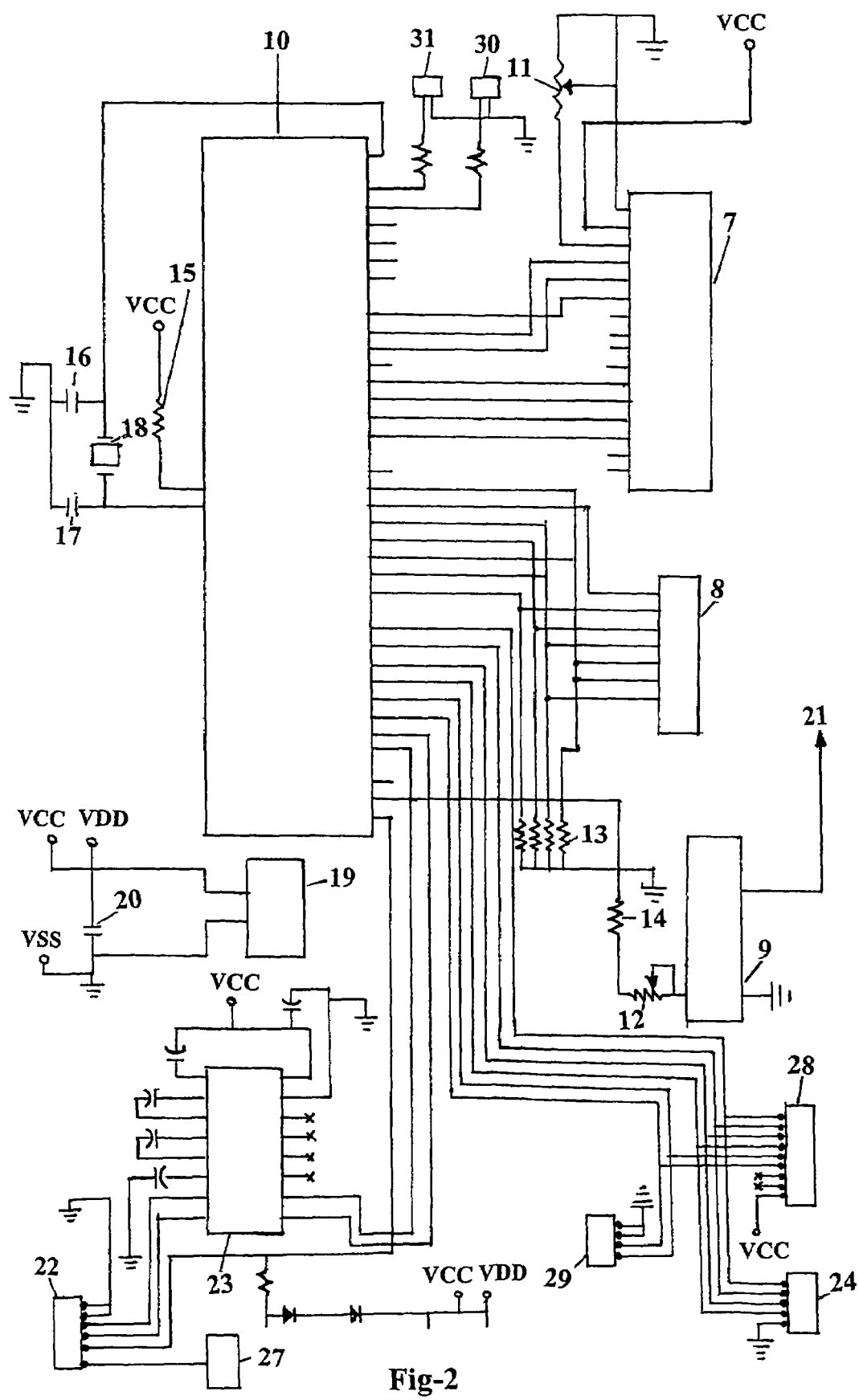
FIG. 2 shows a schematic diagram of the electronic circuit of the device where in accordance with the present invention comprises an alternating current output, one microcontroler, a liquid crystal display (LCD), a keyboard or a programmable integrated circuit, a serial port, an integrated circuit to interface the microcontroller to a computer, resistors, capacitors, multiposition rotary timing switch, potentiometers and a power source or a power supply battery of 6 Volts.

The detailed description of the preferred embodiments and drawings herein after being made by reference to the accompanying drawings, does not intend to limit the scope of the invention, and it will be readily understood by one skilled in the art that the present invention is not anticipated by the prior art.

One way of application of the invention is described by reference to the included figures.

The electronic device consists of five groups of spiral form coils (1) printed on flexible plastic plates.

The group (2) consists of up to 52 coils. The groups (3) and (4) consist of up to 12 coils each one, the group (5) consists of up to 20 coils and the group (6) consists of up to 24 coils. These groups cover completely the five different regions of the skull and are in hemispheric arrangement inside one helmet or plane arrangement on the surface of a flexible plastic plate. The end (21) of all coils (1) is connected in parallel through resistors with the alternating current output (9) and the other common end of all coils is grounded. All coils are supplied with the same current intensity and produce simultaneously alternating magnetic fields of positive square wave symmetrical signal with 50% duty cycle of the same intensity and frequency. The coils are made by a good conductive metal and are printed on flexible plates. The diameter of the coils (1) can be from 0.5 cm up to 2.5 cm. The device comprises also one microcontroler (10) as an integrated circuit which recognizes and works out the data given by the key board type matrix (8) or a programmable circuit (29) or other button, for programming alternating current with frequency and shape which are produced by microcontroller (10) according to the data given by the computer (27) for frequency programming using the appropriate program through the serial port (22) used for operation frequency programming and the interface integrated circuit (23) to the microcontroler (10), one Liquid Crystal Display (LCD) (7) for interface, the potentiometer (11) to regulate the contrast of the Liquid Crystal Display (LCD) and the potentiometer (12) to regulate the intensity of the alternating current which is a function of the intensity of the magnetic fields so that to have the same value with the intensity determined by the multi channel biomagnetometer for the examined individual. The operation time of the device is regulated by a multiposition or a rotary timing switch (24) through the microcontroller (10). The resistances (28) as a pull up resistor with common end with the electric source connect in parallel the programmable circuit (29) with the rotary timing switch (24) and the microcontroller (10).

The device comprises also pull-down resistors (13) to increase the potential, the resistors (14) and (15) and also capacitors (16) and (17) for crystal oscillator operation and the time operation crystal (18) for the timing frequencies of the system. The resistances are ranged from several tens of Ohm up to several tens of kOhm and the capacitance of the capacitors is ranged from several pFarad up to several nFarad. Finally the device comprises an electrical DC power supply or battery from +5V up to +12V (19) with two diodes in series to drop the total Voltage. The microcontroller (10) controls also the good function of the device by indicating LED (30) and of the power supply by indicating LED (31).

The microcontroller (10) is using the inside comparator to check the battery level and provided that the battery is in good condition a button is pressed to go to programming mode by which the frequency of the output signal can be changed. If the button is not pressed then the operation time can be defined by the rotary timing switch and a square wave signal at the output pin is produced by the microcontroller (10).

The ions perform spiral trajectories around the magnetic lines of the alternating magnetic field which is emitted from the coils (1), which are placed in such a way so that the orientation of some part of the magnetic lines to coincide with the flow of the blood plasma, so that the charged plasma ions in the brain to move in spiral form around those parts of the magnetic lines which are parallel to the flow of blood plasma. During the change in direction of the magnetic field the ions are forced to change direction of rotation. These abrupt changes, which are done usually with the alternating magnetic fields of square wave form, cause friction of the plasma ions with calcium and other inorganic substances which are placed on the pineal gland and other brain centers, so that to break the connection binding of the calcium atoms and to remove those atoms from the brain glands.

The Biomagnetometer of superconductive quantum interference is based on Josephson effect of superconductivity which is the following: When two superconductive metals come in touch with one very thin foil of an insulator which is placed between them then electrons are passing through the insulator from one metal to another metal. The flow of electrons, which is known as Josephson current, is interrupted if a constant voltage is applied between the two metals and the electrons start to flow again with the application of an alternating voltage of high frequency. When two superconductive metals with a horseshoe shape come in touch with two thin insulator foils then two Josephson currents appeared which are interfered between them. If in the neighborhood of these metals there is an alternating magnetic field then it is possible to measure the Josephson current as a function of the alternating magnetic field. On this principle is based the construction of the superconductive quantum interference device with which it is possible to measure very small alternating magnetic fields of the order of few pTesla.

The biomagnetometer consists from one or more receiving antennas, one container for the liquid He(−269° C.) and the necessary electronics. The signal is analysed by linear and nonlinear methods to come to the conclusions about the operational functions of various organs of the body.

The invention claimed is:

1. A device for strengthening the immune system in a human being comprising: an electronic multi channel biomagnetometer used to produce magnetic fields which includes a plurality of coils for producing alternating magnetic fields when supplied with electrical current, said coils being applied on a flexible material wherein said coils are divided into five groups which are spaced such that the groups are adapted to overlay separate areas of a person's brain when the material is placed in proximity to the person's brain;

an alternating current output connected to said coils for producing alternating magnetic fields;

a microcontroller connected to said alternating current output for controlling current from said alternating current output;

a programmable circuit for programming said microcontroller to vary a frequency and shape of the alternating current from the alternating current output from data obtained from a computer, a display for indicating operating characteristics of said electronic multi channel biomagnetometer;

a timing switch to regulate an operational timing of said microcontroller; and a power source.

2. The device of claim 1 wherein said five groups of said coils are further defined as being placed in a hemispheric array such that a first group is arranged to overlay a vertex region of a person's skull and consists of 1 to 52 of said coils, a second group is arranged to overlay a frontal region of the skull and consists of 1 to 12 of said coils, a third group is arranged to overlay a occipital region of the skull and consists of 1 to 12 of said coils, a fourth group is arranged to overlay a left side of the skull and consists of 1 to 26 of said coils and a fifth group is arranged to overlay a right side of the skull and consists of 1 to 20 of said coils.

3. The device of claim 1 wherein said coils are made of a conductive metal.

4. The device of claim 1 wherein said coils are arranged in a hemispherical array inside a helmet designed to cover completely five regions of a person's skull including a vertex, frontal, occipital, right, and left regions of the skull.

5. The device of claim 1 wherein said coils are defined by two ends, a first end of said coils are connected in parallel and wherein a second end of each of said coils is grounded.

6. The device of claim 1 wherein said alternating current output produces alternating and positive symmetrical square wave signals.

7. The device of claim 6 wherein said programmable circuit and said microcontroller vary current from the alternating current output to produce magnetic fields of low frequencies in a range of from 1 to 20 Hertz and wherein the magnetic fields can be adjusted according to a frequency and intensity determined during a diagnostic process of said multi channel biomagnetometer device such that the frequency and the intensity are adapted to be adjusted to cause charged blood ions in the brain to rotate in spiral trajectories around the magnetic fields.

8. The device of claim 1 wherein said power source includes a battery.

9. The device of claim 1 includes only one of said alternating current output is of such as to supply a square wave signal and wherein said square wave signal is of a frequency of a range of 1 to 20 Hertz and wherein said alternating current output is connect to up to 122 of said coils.

10. The device of claim 1 wherein said microcontroller further includes an integrated circuit and wherein said integrated circuit recognizes and works out data obtained from a keyboard and said programmable circuit such that said alternating current output has a current with frequency and shape which are produced from said microcontroller to regulate the characteristics of the magnetic fields.

11. The device of claim 10 wherein said microcontroller accepts data given by said computer to program said frequency through a serial port.

12. The device of claim 1 wherein said display is a Liquid Crystal Display (LCD) and provides an optical indication of the frequency and the intensity of the magnetic fields.

13. The device of claim 1 wherein resistors are placed between said coils.

14. The device of claim 1 wherein a potentiometer regulates the intensity of said alternating current output to a function of an intensity of the magnetic fields to a value based on an intensity determined by said multichannel biomagnetometer for an examined individual.

15. The device of claim 1 wherein said timing switch is a rotary switch which regulates operation time of said multi channel biomagnetometer.

16. The device of claim 1 wherein said display includes Liquid Crystal Display elements to check a level of power of said power source.

17. The device of claim 1 including a serial port for operation frequency programming and an interface integrated circuit which connect said computer with said microcontroller, and a pull up resistor connecting common ends of said programmable circuit, said timing switch, and said microcontroller and said potentiometer in parallel.

18. A device for charging plasma ions in a person's brain to move in spiral trajectories by alternately changing magnetic fields to thereby cause friction to break bonds of calcium and other similar chemical elements found in glands of the brain to allow removal of the calcium and the other similar chemical elements from the glands to promote better inhibitory hormone production thereby strengthening the immune system, the device including:

an electronic multi channel biomagnetometer used to produce magnetic fields which includes a plurality of coils for producing alternating magnetic fields when supplied with electrical current in a picoTesla (pT) range, said coils being applied on a flexible material wherein said coils are divided into groups which are spaced such that the groups are adapted to overlay separate areas of a person's body when the material is placed in proximity to the person's body;

an alternating current output connected to said coils for producing alternating magnetic fields;

a microcontroller connected to said alternating current output for controlling current from said alternating current output;

a programmable circuit for programming said microcontroller to vary a frequency and shape of the alternating current from the alternating current output from data obtained from a computer, a display for indicating operating characteristics of said electronic multi channel biomagnetometer;

a timing switch to regulate an operational timing of said microcontroller; and a power source.

* * * * *